(12) United States Patent
Kayan

(10) Patent No.: US 7,169,157 B2
(45) Date of Patent: Jan. 30, 2007

(54) TACKING TOOL AND TACK

(75) Inventor: Helmut Kayan, Redwood City, CA (US)

(73) Assignee: Tyco Healthcare Group LP, North Haven, CT (US)

( * ) Notice: Subject to any disclaimer, the term of this patent is extended or adjusted under 35 U.S.C. 154(b) by 595 days.

(21) Appl. No.: 10/418,404

(22) Filed: Apr. 17, 2003

(65) Prior Publication Data

US 2003/0236534 A1 Dec. 25, 2003

Related U.S. Application Data

(60) Provisional application No. 60/373,710, filed on Apr. 17, 2002.

(51) Int. Cl.
- *A61B 17/08* (2006.01)
- *A61B 17/04* (2006.01)
- *B21F 9/00* (2006.01)

(52) U.S. Cl. .............. 606/148; 606/144; 140/123.6

(58) Field of Classification Search .......... 606/74, 606/103, 113, 116, 129, 144, 148; 140/71 R, 140/88, 92, 93 R, 93 A, 102, 102.5, 123, 140/123.6, 139

See application file for complete search history.

(56) References Cited

U.S. PATENT DOCUMENTS

| | | | |
|---|---|---|---|
| 3,435,526 A | 4/1969 | Brancato | |
| 3,638,654 A | 2/1972 | Akuba | |
| 3,858,783 A | 1/1975 | Kapitanov et al. | |
| 3,870,048 A | 3/1975 | Yoon | |
| RE28,932 E | 8/1976 | Noiles et al. | |
| 4,204,541 A | 5/1980 | Kapitanov | |
| 4,235,246 A | 11/1980 | Weiss | |
| 4,306,560 A * | 12/1981 | Harris | 606/129 |
| 4,357,946 A | 11/1982 | Dutcher et al. | |
| 4,406,363 A | 9/1983 | Aday | |
| 4,448,194 A | 5/1984 | DiGiovanni et al. | |
| 4,593,843 A | 6/1986 | Saravis | |
| 4,595,007 A | 6/1986 | Mericle | |
| 4,596,350 A | 6/1986 | Smith et al. | |
| RE32,227 E | 8/1986 | Dutcher | |
| 4,616,638 A | 10/1986 | Griggs | |
| 4,627,437 A | 12/1986 | Bedi et al. | |
| 4,628,943 A | 12/1986 | Miller | |
| 4,643,190 A | 2/1987 | Heimberger | |
| 4,850,355 A | 7/1989 | Brooks et al. | |
| 4,858,601 A | 8/1989 | Glisson | |
| 4,950,276 A | 8/1990 | Vince | |
| 4,976,715 A | 12/1990 | Bays et al. | |
| 5,007,921 A | 4/1991 | Brown | |
| 5,018,530 A | 5/1991 | Rank et al. | |
| 5,053,047 A | 10/1991 | Yoon | |
| 5,100,420 A | 3/1992 | Green et al. | |
| 5,171,247 A | 12/1992 | Hughett et al. | |

(Continued)

FOREIGN PATENT DOCUMENTS

BE 1006874 A6 1/1995

(Continued)

Primary Examiner—Julian W. Woo

(57) ABSTRACT

A surgical tacking apparatus for forming and applying surgical fasteners during laparoscopic or endoscopic procedures is disclosed. It includes a housing having a handle, an elongated tubular portion extending from the housing, a wire advancer, and a wire shaping nose at its distal end. An annular fastener is also disclosed.

15 Claims, 3 Drawing Sheets

U.S. PATENT DOCUMENTS

| | | |
|---|---|---|
| 5,171,249 A | 12/1992 | Stefanchik et al. |
| 5,203,864 A | 4/1993 | Phillips |
| 5,217,486 A | 6/1993 | Rice et al. |
| 5,221,269 A * | 6/1993 | Miller et al. ................ 606/116 |
| 5,222,976 A | 6/1993 | Yoon |
| 5,228,565 A | 7/1993 | Sinn |
| 5,242,457 A | 9/1993 | Akopov et al. |
| 5,258,000 A | 11/1993 | Gianturco |
| 5,259,395 A | 11/1993 | Li |
| 5,269,792 A | 12/1993 | Kovac et al. |
| 5,271,543 A | 12/1993 | Grant et al. |
| 5,282,807 A | 2/1994 | Knoepfler |
| 5,295,956 A | 3/1994 | Bales et al. |
| 5,297,714 A | 3/1994 | Kramer |
| 5,306,281 A | 4/1994 | Beurrier |
| 5,309,617 A | 5/1994 | Dannar |
| 5,309,927 A | 5/1994 | Welch |
| 5,312,024 A | 5/1994 | Grant et al. |
| 5,318,575 A | 6/1994 | Chesterfield et al. |
| 5,320,630 A | 6/1994 | Ahmed |
| 5,330,503 A | 7/1994 | Yoon |
| 5,354,292 A | 10/1994 | Braeuer et al. |
| 5,356,064 A | 10/1994 | Green et al. |
| 5,356,424 A | 10/1994 | Buzerak et al. |
| 5,382,260 A | 1/1995 | Dormandy, Jr. et al. |
| 5,411,522 A | 5/1995 | Trott |
| 5,417,700 A | 5/1995 | Egan |
| 5,433,721 A | 7/1995 | Hooven et al. |
| 5,437,266 A | 8/1995 | McPherson et al. |
| 5,439,156 A | 8/1995 | Grant et al. |
| 5,452,836 A | 9/1995 | Huitema et al. |
| 5,454,834 A | 10/1995 | Boebel et al. |
| 5,465,895 A | 11/1995 | Knodel et al. |
| 5,487,500 A | 1/1996 | Knodel et al. |
| 5,488,958 A | 2/1996 | Topel et al. |
| 5,499,990 A | 3/1996 | Schülken et al. |
| 5,500,001 A | 3/1996 | Trott |
| 5,501,683 A | 3/1996 | Trott |
| 5,545,148 A | 8/1996 | Wurster |
| 5,582,616 A | 12/1996 | Bolduc et al. |
| 5,607,436 A | 3/1997 | Pratt et al. |
| 5,626,613 A | 5/1997 | Schmieding |
| RE35,525 E | 6/1997 | Stefanchik et al. |
| 5,662,683 A | 9/1997 | Kay |
| 5,728,116 A | 3/1998 | Rosenman |
| 5,772,668 A | 6/1998 | Summers et al. |
| 5,782,844 A | 7/1998 | Yoon et al. |
| 5,797,931 A | 8/1998 | Bito et al. |
| 5,810,851 A | 9/1998 | Yoon |
| 5,810,882 A | 9/1998 | Bolduc et al. |
| 5,824,008 A | 10/1998 | Bolduc et al. |
| 5,830,221 A | 11/1998 | Stein et al. |
| 5,833,695 A | 11/1998 | Yoon |
| 5,904,696 A | 5/1999 | Rosenman |
| 5,941,890 A | 8/1999 | Voegele et al. |
| 5,964,772 A | 10/1999 | Bolduc et al. |
| 5,989,268 A | 11/1999 | Pugsley, Jr. et al. |
| 6,036,701 A | 3/2000 | Rosenman |
| 6,063,070 A | 5/2000 | Eder |
| 6,099,537 A | 8/2000 | Sugai et al. |
| 6,113,611 A | 9/2000 | Allen et al. |
| 6,261,302 B1 | 7/2001 | Voegele et al. |
| 6,296,656 B1 | 10/2001 | Bolduc et al. |
| 6,402,765 B1 | 6/2002 | Monassevitch et al. |
| 6,425,903 B1 | 7/2002 | Voegele |
| 6,511,489 B2 * | 1/2003 | Field et al. ................ 606/148 |
| 6,527,785 B2 * | 3/2003 | Sancoff et al. ............. 606/148 |
| 6,551,332 B1 | 4/2003 | Nguyen et al. |
| 6,551,333 B2 | 4/2003 | Kuhns et al. |
| 6,564,806 B1 * | 5/2003 | Fogarty et al. ............. 606/116 |
| 6,679,895 B1 * | 1/2004 | Sancoff et al. ............. 606/148 |
| 6,767,352 B2 * | 7/2004 | Field et al. ................ 606/148 |
| 2002/0065524 A1 | 5/2002 | Miller et al. |
| 2002/0068947 A1 | 6/2002 | Kuhns et al. |
| 2002/0087170 A1 | 7/2002 | Kuhns et al. |
| 2003/0105473 A1 | 6/2003 | Miller |

FOREIGN PATENT DOCUMENTS

| | | |
|---|---|---|
| DE | 295962 | 5/1916 |
| DE | 4304353 A1 | 4/1994 |
| EP | 0121362 A1 | 10/1984 |
| EP | 0324166 A2 | 7/1989 |
| EP | 0442482 A2 | 8/1991 |
| EP | 0554653 A2 | 8/1993 |
| EP | 0645149 A1 | 3/1995 |
| EP | 0648471 A1 | 4/1995 |
| EP | 0663184 A1 | 7/1995 |
| EP | 686373 A1 | 12/1995 |
| FR | 320731 | 4/1902 |
| FR | 2299548 | 8/1976 |
| FR | 2377796 | 8/1978 |
| GB | 2148232 A | 5/1985 |
| WO | WO90/14795 | 12/1990 |
| WO | WO93/16644 | 9/1993 |
| WO | WO96/03925 | 2/1996 |

* cited by examiner

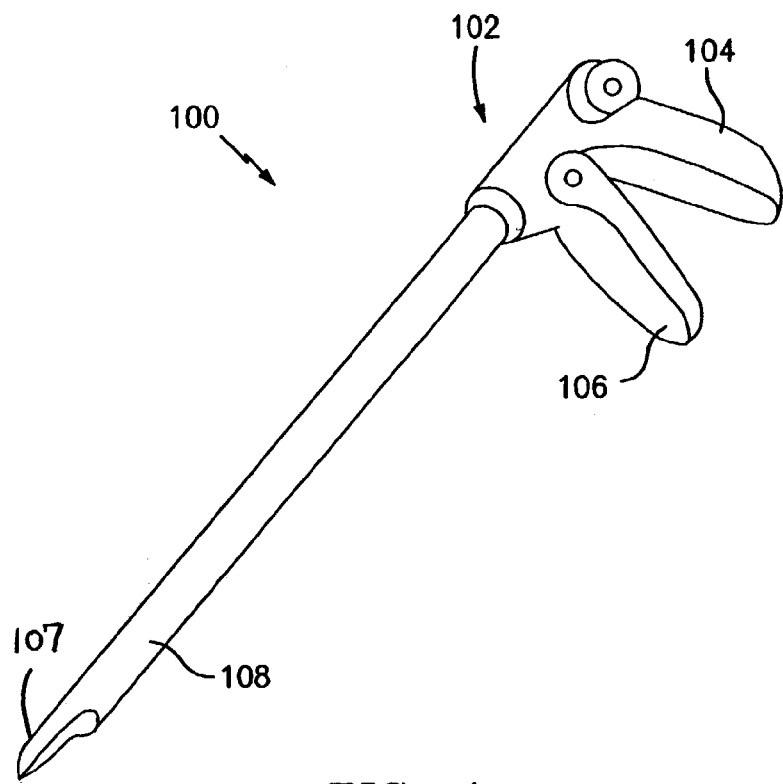
*FIG. 1*
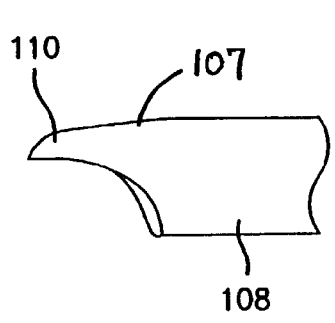
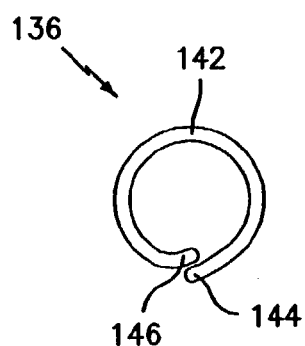
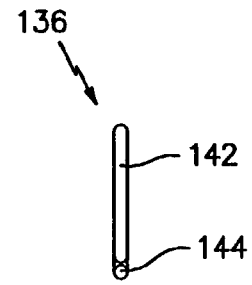
*FIG. 2*     *FIG. 4*     *FIG. 5*

TACKING TOOL AND TACK

CROSS REFERENCE TO RELATED APPLICATIONS

This application claims priority from and the benefits of U.S. provisional application No. 60/373,710 filed on Apr. 17, 2002.

BACKGROUND

1. Technical Field

The present disclosure relates generally to surgical apparatus for fastening objects to body tissue and, more particularly, to a surgical tacking tool configured to apply a loop fastener to a surgical mesh and underlying tissue during surgical procedures to repair body tissue, such as hernia repair.

2. Background of Related Art

A number of surgical procedures require instruments that are capable of applying a surgical fastener to tissue in order to form tissue connections or to secure objects to tissue. For example, during hernia repair it is often desirable to fasten a surgical mesh to the underlying body tissue. In certain hernias, such as direct or indirect inguinal hernias, a part of the intestine protrudes through a defect or an opening in the supporting abdominal wall to form a hernial sac. The opening can be repaired using an open surgery procedure in which a relatively large incision is made in the patient and the hernia is closed off outside the abdominal wall by suturing. Alternatively, a mesh is attached with sutures over the opening to provide reinforcement.

Less invasive surgical procedures are currently available for hernia repair. In laparoscopic procedures, surgery is performed in the abdomen through a small incision, while in endoscopic procedures surgery is performed through narrow endoscopic tubes inserted through small incisions in the body. Laparoscopic and endoscopic procedures generally require long and narrow instruments capable of reaching deep within the body and configured to form a seal with the incision or tube through which they are inserted.

Currently, endoscopic techniques for hernia repair utilize fasteners, such as surgical staples or clips, to secure the mesh to the tissue in order to provide reinforcement to the repair and in order to provide structure for encouragement of tissue ingrowth. These staples or clips need to be compressed against the tissue and mesh in order to secure the two together thereby requiring a tool which is positioned on each side of the mesh and tissue in order to deform the staple or clip. Another type of fastener suited for use in affixing mesh to tissue, during procedures such as hernia repair, is a coil fastener having a helically coiled body portion terminating in a tissue penetrating tip, which helical fastener is screwed into the mesh and body tissue. An example of this type of fastener is disclosed in U.S. Pat. No. 5,258,000. Thus, the need exists for an improved surgical fastening apparatus that applies a fastener to surgical mesh and body tissue for effectively securing the mesh to the body tissue.

It is an object of the present disclosure to provide a tacking tool for securing a tack to both surgical mesh and body tissue.

Another object of the present disclosure is to provide a tacking tool that can apply a tack linearly to both surgical mesh and body tissue.

SUMMARY

This invention is directed to a tacking apparatus for applying fasteners to body tissue that includes a housing, an actuation mechanism, a supply of an elongated wire, an elongated tubular portion having a proximal end and a distal end, the proximal end being in communication with the housing, and the distal end having a nose having an interior portion adapted for shaping a length of the wire into an annular shape, a wire advancer for advancing the wire from the supply to and through the nose portion of the elongated tubular portion, the wire advancer being actuated by the actuation mechanism and cooperable with the wire shaping portion of the nose to shape the length of the wire into a annular shape, and a cutter for severing the annular shaped portion of the wire to form an annular fastener. The actuation mechanism can include a trigger operatively coupled to the housing. In one preferred embodiment, the interior portion of the nose can be concavely curved or may have a semi-circular configuration. The fastener can have a body that is substantially planar. The interior portion of the nose can be shaped to provide a fastener with an inwardly disposed end, and an outwardly disposed end that overlaps the inwardly disposed end. The cutter may be operatively coupled to the actuation mechanism, it can be adapted to provide the inwardly disposed end of the fastener with a sharp tip, and it may be adapted to sever the length of wire at or near the distal end of the nose of the tubular portion, to thereby form the annular fastener. Further still, the supply of wire can be a spool having an endless length of the wire wound thereon for providing a multitude of fasteners. The wire can be formed from a shape memory material. The tubular portion can be adapted to fit through a body incision for a laparoscopic procedure. The nose can include a divider having a channel to pass the wire to the shaping portion in the nose.

The invention is also directed to a tack for fastening surgical mesh to body tissue. The tack can include a biocompatible substantially planar annular wire body, the body having a first end and a second end, the first end being disposed inwardly of the second end and having a tip suitable for penetrating body tissue, and the second end being disposed outwardly of and overlapping the first end. The first end of the tack may be sharpened. In another embodiment of the tack, the wire may be formed from either a shape memory material or a bioabsorbable material.

BRIEF DESCRIPTION OF THE DRAWINGS

By way of example only, preferred embodiments of the disclosure will be described with reference to the accompanying drawings, in which:

FIG. 1 is a perspective view of a preferred embodiment of a surgical tacking tool according to the present disclosure;

FIG. 2 is an enlarged perspective view of the distal tip of the surgical tacking tool shown in FIG. 1;

FIG. 4 is a front elevational view of a wire ring formed by the surgical tacking tool shown in FIG. 1;

FIG. 5 is a side elevational view of the wire ring shown in FIG. 4; and

DETAILED DESCRIPTION OF PREFERRED EMBODIMENTS

Figure 3:
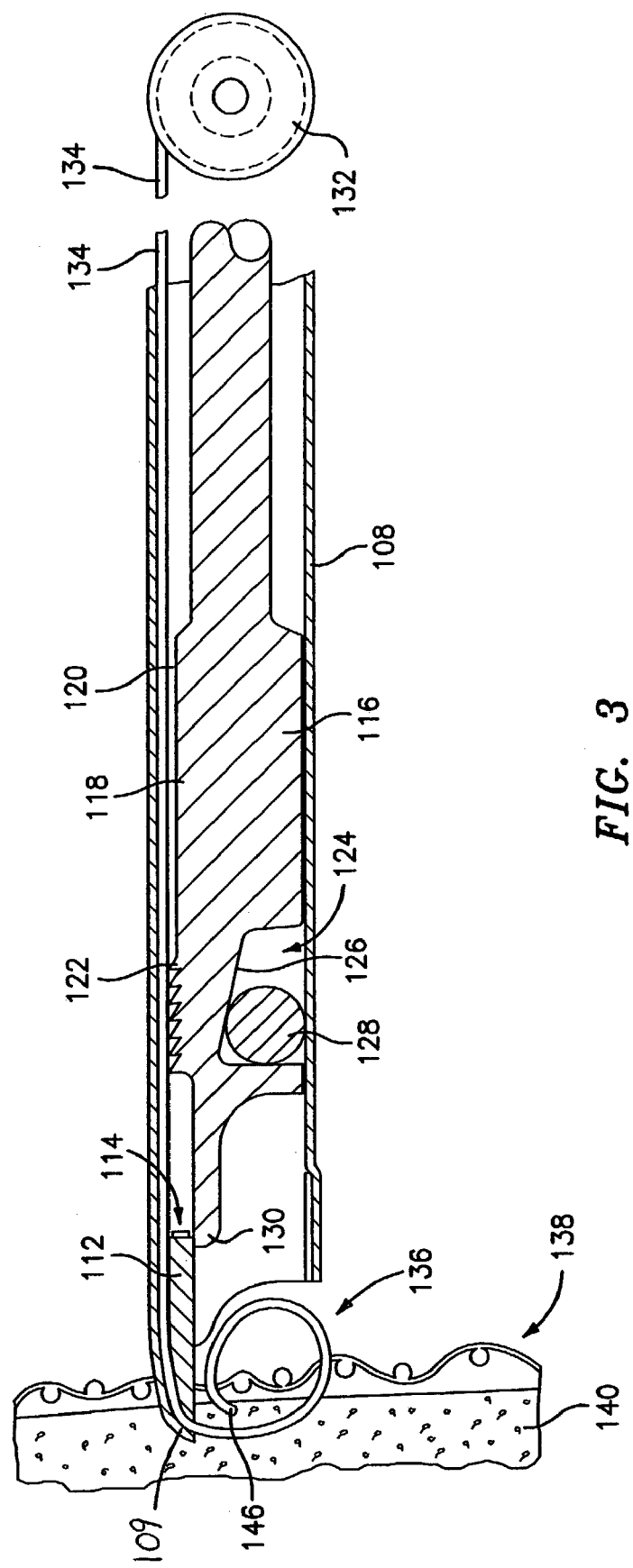
FIG. 3 is a cross-sectional side elevational view with portions broken away as would be taken through a portion of the surgical tacking tool of FIG. 1.

Referring now in detail to FIGS. 1–3, in which like reference numerals identify similar or identical elements, a surgical tacking apparatus or tool in accordance with the present disclosure is generally designated as 100. As used herein, the term "distal" refers to that portion of the tool, or component thereof which is further from the user while the term "proximal" refers to that portion of the tool or component thereof which is closer to the user.

Tacking tool 100 is configured to apply a ring fastener to tissue or to secure surgical mesh to tissue during surgical procedures such as hernia repair. Tacking tool 100 generally includes a housing 102 including a handle portion 104 extending from the housing 102. Tacking tool 100 includes an actuation mechanism, e.g. a trigger 106 pivotally connected to housing 102, with a free end of trigger 106 being spaced from a free end of handle 104. Tacking tool 100 also includes an elongated tubular portion 108 extending distally from housing 102. Elongated tubular portion 108 is preferably dimensioned to fit through conventional laparoscopic incisions and respective 15 mm, 10 mm, and 5 mm trocar cannula structures. As seen in FIG. 2, a distal end 107 of the tubular portion 108 is provided with a hollow down turned semi-circular or arcuate nose 110 oriented along the longitudinal axis of tubular portion 108. Nose 110 preferably includes a divider 112 defining a channel 114 therethrough for channeling wire 132 to nose 110 (see FIG. 3).

Turning now to FIG. 3, the internal structure of elongated tubular portion 108 is shown in detail. Elongated tubular portion 108 includes a reciprocable wire advancer 116 internally disposed therewithin. Wire advancer 116 includes an elongated shaft, here shown as having a substantially circular body portion with an elongated flattened, or otherwise shaped surface portion 118 that defines a passage 120 between an inner surface of tubular portion 108 and wire advancer 116. Wire advancer 116 includes structure for engaging and distally advancing wire 134, for example a plurality of teeth 122 formed along the periphery of wire advancer 116, preferably distally of flattened surface portion 118. While it is preferred that teeth 122 are formed near the distal end of wire advancer 116, it is envisioned that teeth 122 can be formed at any suitable location on or along wire advancer 116. The wire may be advanced by other gripping or friction enhancing structures. These structures can be static, movable, rotatable, ratchet-like, indexing, etc. Preferably, wire advancer 116 is provided with a chamber 124 preferably in substantial transverse alignment with teeth 122, chamber 124 being opened along a side radially opposite to flattened surface 118 of wire advancer 116. Chamber 124 defines an elongated centrally disposed camming surface 126 that is more deeply internally or centrally disposed within wire advancer 116 near the surface's distal end and than its proximal end. A bearing structure 128 is disposed within chamber 124. Bearing structure 128 is sized to contact camming surface 126 near its distal end and to contact the inner surface of tubular portion 108. In this manner, as wire advancer 116 is advanced through elongated tubular portion 108, camming surface 126 rides along bearing structure 128 thereby pressing advancer 116 and teeth 122 oppositely, radially outward toward the inner surface of tubular portion 108. Although chamber 124 of this embodiment is shown disposed substantially transversely aligned with teeth 122, it is envisioned that chamber 124 can be formed at any suitable location along the length of wire advancer 116 to effect engagement and advancement of wire 134. In addition, while a ball-like bearing structure is shown which is free to rotate longitudinally distally and proximally, it is envisioned that any shaped bearing structure, fixed or relatively moveable, can be employed.

Elongated tubular portion 108 includes a cutter. Preferably, wire advancer 116 includes the cutter, 130, extending distally therefrom. Cutter 130 is configured and adapted for slidable engagement preferably along an elongated surface of divider 112 as wire advancer 116 is advanced distally through tubular portion 108. FIG. 3 shows wire advancer 116 in a proximal position. As cutter 130 moves distally along the distal end portion of divider 112, at or adjacent down turned nose 110 of tubular portion 108, cutter 130 shears through wire 134, preferably where or near where it projects out of channel 114. Preferably, the shearing action forms a distal end 146 that facilitates ease of entry into the tissue. Preferably, distal end 146 is sharpened.

Tacking tool 100 includes a replaceable wire source or supply, here shown as wire spool 132 located within handle portion 104 and operatively coupled to wire advancer 116. Wire spool 132 is provided with a straight "endless" surgical grade wire 134 wound thereon. By "endless" it is meant that wire 134 has ends, but is very long to provide a multitude of fasteners without replacing wire spool 132. Wire 134 is threaded through tubular portion 108 by passing wire 134 through passage 120, over teeth 122, preferably at least into channel 114. From there, prior to use, wire 134 can be advanced further into channel 114, and prior to or even with the edge of nose 110 of tubular portion 108. In operation, wire advancer 116 is moved distally through tubular portion 108, such that camming surface 126 rides along bearing surface 128 and causes teeth 120 to grip wire 134, thereby advancing a selected portion or length of wire 134 through tubular portion 108 and out through nose 110. As wire 134 is advanced along and out of nose 110, the interior concave portion 109 of nose 110, deforms wire 134 and causes it to turn arcuately 360° or more in onto itself forming an annular fastener, here shown as a wire loop or ring 136 (FIG. 4). Finally, as wire advancer 116 is advanced to its most distal position, cutter 130 shears through wire 134 preferably at or near where it exits channel 114, thereby separating wire ring 136 from the remainder of wire 134. As seen in FIG. 3, prior to or as wire 134 is being advanced, nose 110 of tacking tool 100 is pressed into a suitable surgical mesh 138 and into underlying tissue 140. Thus, as wire ring 136 is formed, it fastens surgical mesh 138 to the underlying tissue 140. While wire 134 has been disclosed as being a straight wire wound on a spool, it is envisioned that a wire formed from a shape memory material and having a shape memory, e.g. Nitinol, can be used, which shape memory wire will automatically cause the wire to curve as it is ejected through nose 110 of tubular portion 108. If shape memory wire is employed that is restrained and predetermined to curve and form a ring as it is freed from a restraint, a curved nose may not be needed. The same applies if a temperature triggerable shape memory metal is employed and the tacking tool is employed at the triggering temperature, for example, by use of body tissue temperature. It will be understood that wire 134 can be made of any suitable biocompatible material, for example, metals, metal alloys, shape memory or not, and polymeric materials, preferably bioabsorbable.

As shown in FIG. 3, to apply wire ring 136, nose 110 of tubular portion 108 is inserted into tissue 140 through mesh 138. Wire 134 is then advanced through tubular portion 108 and out of nose 110, beginning the formation of ring 136. As more wire 134 is advanced through nose 110, more of ring 136 is formed. As ring 136 is formed, a first, inwardly disposed end 146 of wire 134 first penetrates through tissue 140, and follows an arcuate path as it exits tissue 140, passes into the underside of surgical mesh 138, and then distally back through surgical mesh 138 and back into tissue 140, thereby completing the formation of wire ring 136 and the fastening of mesh 138 to tissue 140.

In a preferred embodiment, one complete squeeze of trigger 106 will result in the formation of a complete wire ring 136. In order to ensure that a complete wire ring 136 is formed with the squeezing of trigger 106, preferably a latch and pawl mechanism (not shown) is provided in the handle 102. In operation, as trigger 106 is squeezed wire advancer 116 is moved distally through tubular portion 108 thereby commencing the formation of wire ring 136. Once trigger 106 is depressed slightly, the latch and pawl mechanism is configured to prohibit trigger 106 from backstroking until trigger 106 has been completely depressed and wire ring 136 is completely formed. Upon complete depression of trigger 106, the pawl clears the gear teeth (not shown) and the pawl rotates away from the teeth due to a spring biasing (not shown), thereby allowing trigger 106 to return to its unsqueezed or undepressed condition.

Upon complete depression of trigger 106, wire advancer 116 travels a predetermined distance through tubular portion 108, causing wire 134 to be ejected a predetermined amount or length which is substantially equal to the circumference of wire ring 136 thereby resulting in the formation of a complete wire ring 136. Moreover, where trigger 106 is only partially depressed, the spring-loaded pawl (not shown) operates to hold trigger 106 stationary and will continue to function to hold trigger 106 stationary until trigger 106 has been completely depressed. In this way, the formation of wire ring 136 into body tissue 140 and surgical mesh 138 is controlled so that a single wire ring 136 at a time may be completely formed and fastened to body tissue 140 and surgical mesh 138. The above arrangement prevents formation of only partly formed fasteners.

In FIGS. 4 and 5, wire ring 136 is further shown and described. Wire ring 136 includes a body portion 142 preferably having a first, inwardly disposed end 146 and a second outwardly disposed trailing end 144. As seen in FIG. 4, after formation of a complete wire ring 136, sharpened end 146 underlaps (laps radially inside of) second trailing end 144. It is envisioned, however, that depending on the radius and extent or length of curvature of the shaping portion of nose 110 of tubular portion 108, trailing end 144 can be made to overlap leading end 146, or leading end 146 can be made to overlap trailing end 144. As seen in FIG. 5, after complete formation, wire ring 136 is substantially planar (i.e., proximal end 144 and distal end 146 lie on the same plane with one another). Further, it is seen in FIG. 5 that wire 134 making up wire ring 136 has a circular cross section. However, it is envisioned that any suitable cross-sectional shape or configuration of the wire can be used to form wire ring 136 although a wire having a cross section without sharpened edges is preferred in order to eliminate the possibility of the sharpened edges cutting into the tissue or cutting through the surgical mesh.

Figure 6:
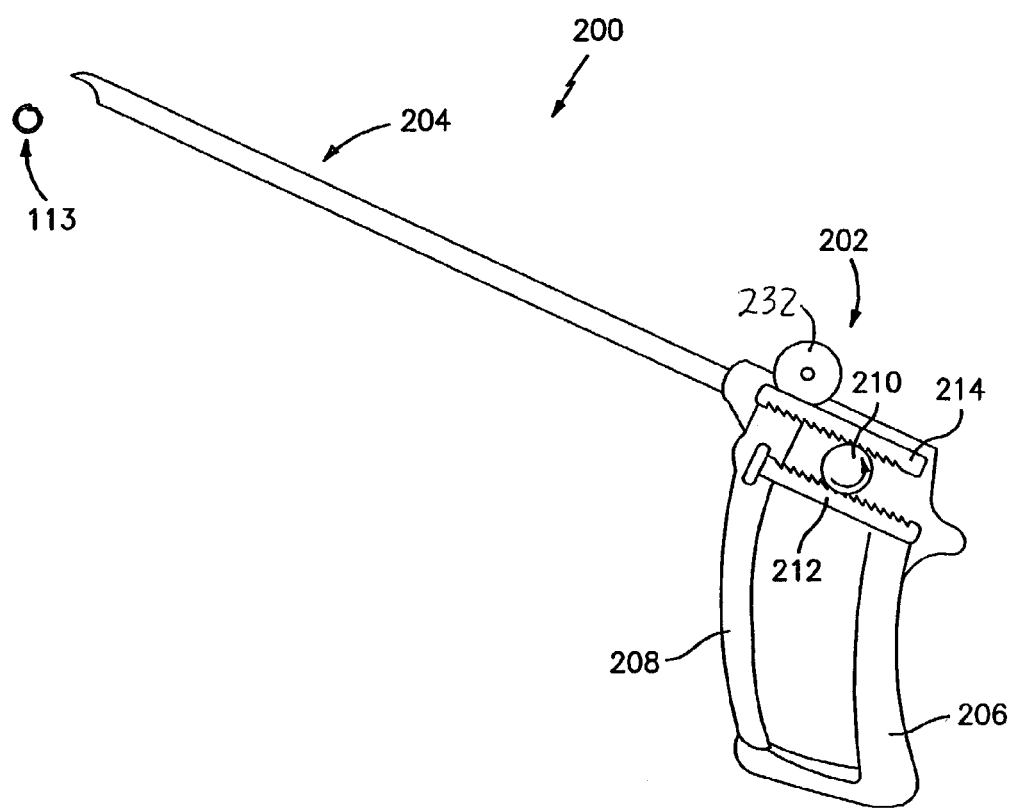
FIG. 6 is a perspective view of an alternative embodiment of a housing portion for a surgical tacking tool in accordance with the present disclosure.

Turning now to FIG. 6, an alternative embodiment of a tacking tool according to the present disclosure is generally shown as 200. Tacking tool 200 includes a handle or a housing 202 and a tubular portion 204 projecting from a distal end thereof. The housing 202 includes a handle portion 206 and a trigger 208 slidably coupled thereto and spaced a distance from the handle portion 206. Housing 202 further includes a dual rack and pinion arrangement wherein a pinion 210 is pivotably coupled to housing 202, a lower rack 212 is pivotably coupled to the trigger 208 and slidably coupled to the handle portion 206, and an upper rack 214 being slidably coupled to housing 202 and rigidly coupled to wire advancer 116 (not shown in FIG. 6, see FIG. 3). In this manner, as trigger 208 is depressed, lower rack 212 is moved proximally thereby rotating pinion 210 counter clockwise which in turn moves upper rack 214 and wire advancer 116 distally. Tacking tool 200 forms a wire ring 136 in the same manner as tacking tool 100.

Tacking tool 200 can be provided with a spool 232 of wire and a latch and pawl mechanism (not shown), like that employed in tacking tool 100, which limits movement of trigger 208 in a distal direction until a complete wire ring 136 is formed, at which time the pawl can be released and trigger 208 allowed to return to its distalmost position.

It is envisioned that the tacking tools disclosed herein can be adapted to be activated and operated remotely, for example robotically. In such instances, for example, the activation mechanism can be located and operated from a remote control box. The same can apply to the wire supply.

It will be understood that various modifications may be made to the embodiments disclosed herein. Therefore, the above description should not be construed as limiting, but merely as an exemplification of preferred embodiments. Those skilled in the art will envision other modifications within the scope and spirit of the claims appended hereto.

What is claimed is:

1. A tacking apparatus for applying fasteners to body tissue comprising:
    a housing;
    an actuation mechanism;
    a supply of an elongated wire;
    an elongated tubular portion having a proximal end and a distal end, the proximal end being in communication with the housing, and the distal end having a nose having an interior portion adapted for shaping a length of the wire into an annular shape;
    a wire advancer for advancing the wire from the supply to and through the nose portion of the elongated tubular portion, the wire advancer being actuated by the actuation mechanism and cooperable with the wire shaping portion of the nose to shape the length of the wire into a annular shape, the wire advancer further including a plurality of teeth that frictionally engage a portion of the wire such that distal movement of the wire advancer advances the wire towards the nose portion; and
    a cutter for severing the annular shaped portion of the wire to form an annular fastener, wherein the cutter is located on a distal portion of the wire advancer.

2. The tacking apparatus of claim 1, wherein the actuation mechanism includes a trigger operatively coupled to the housing.

3. The tacking apparatus of claim 1, wherein the interior portion of the nose is concavely curved.

4. The tacking apparatus of claim 3, wherein the fastener has a body that is substantially planar.

5. The tacking apparatus of claim 4, wherein the interior portion of the nose is shaped to provide a fastener with an inwardly disposed end, and an outwardly disposed end that overlaps the inwardly disposed end.

6. The tacking apparatus of claim 5, wherein the cutter is adapted to provide the inwardly disposed end of the fastener with a sharp tip.

7. The tacking apparatus of claim 1, wherein the interior portion of the nose has a semi-circular configuration.

8. The tacking apparatus of claim 1, wherein the supply of wire is a spool having an endless length of the wire wound thereon for providing a multitude of fasteners.

9. The tacking apparatus of claim 1, wherein the cutter is operatively coupled to the actuation mechanism.

10. The tacking apparatus of claim 1, wherein the wire is formed from a shape memory material.

11. The tacking apparatus of claim 1, wherein the tubular portion is adapted to fit through a body incision for a laparoscopic procedure.

12. The tacking apparatus of claim 1, wherein the cutter is adapted to sever the length of wire at or near the distal end of the nose of the tubular portion, to thereby form the annular fastener.

13. The tacking apparatus of claim 12, wherein the nose includes a divider having a channel to pass the wire to the shaping portion in the nose.

14. The tacking apparatus of claim 1, wherein the wire advancer is slidably disposed in the elongated tubular portion.

15. The tacking apparatus of claim 1, wherein the wire advancer is longitudinally repositionable in the elongated tubular portion.

* * * * *